United States Patent [19]

Hiles et al.

[11] Patent Number: 4,626,604

[45] Date of Patent: Dec. 2, 1986

[54] HYDROGENATION PROCESS

[75] Inventors: Andrew G. Hiles, Pinner, England; John E. Logsdon, Houston, Tex.

[73] Assignee: Davy McKee (London) Limited, London, England

[21] Appl. No.: 774,958

[22] Filed: Sep. 11, 1985

[51] Int. Cl.[4] ............... C07C 29/14; C07C 29/17; C07C 29/132; C11C 3/12

[52] U.S. Cl. .................... 568/881; 549/503; 568/835; 568/857; 585/266; 260/413 CD

[58] Field of Search ............... 568/881, 835, 857; 260/413 R; 549/503; 585/266

[56] References Cited

U.S. PATENT DOCUMENTS

| | | | |
|---|---|---|---|
| 2,549,416 | 4/1951 | Brooks | 568/881 |
| 2,760,994 | 8/1956 | Gwynn | 568/881 |
| 2,771,493 | 11/1956 | Jacks et al. | 568/881 |
| 3,288,866 | 11/1966 | Cooper | 568/881 |
| 3,301,909 | 1/1967 | Kawasaki et al. | 568/881 |
| 4,451,677 | 5/1984 | Bradley et al. | 568/881 |

FOREIGN PATENT DOCUMENTS

| | | | |
|---|---|---|---|
| 1137519 | 12/1982 | Canada | 568/881 |
| 0008767 | 7/1979 | European Pat. Off. | |
| 0074193 | 8/1982 | European Pat. Off. | |
| 3228881 | 2/1984 | Fed. Rep. of Germany | 568/881 |

Primary Examiner—J. E. Evans
Attorney, Agent, or Firm—Bernard, Rothwell & Brown

[57] ABSTRACT

A continuous multi-stage hydrogenation process is described.

This is effected in at least three catalytic stages connected in series. All stages up to and including the penultimate stage are operated adiabatically and in the vapor phase. Aldehyde (or other unsaturated organic compound) is fed to all stages up to and including the penultimate stage. The rate of supply of the aldehyde or other unsaturated organic compound to the penultimate stage is controlled in relation to the catalyst volume in the penultimate catalytic stage so that the degree of hydrogenation in that stage is less than 100%. The remaining chemically unsaturated material in the product mixture from the penultimate stage is hydrogenated, after cooling that product mixture, in the final catalytic stage to produce a substantially completely hydrogenated product mixture. In this way the dwell time of the reactants and product(s) at "hot spot" temperatures is minimized, thus reducing byproduct formation.

30 Claims, 7 Drawing Figures

HYDROGENATION PROCESS

FIELD OF THE INVENTION

This invention relates to a catalytic hydrogenation process.

BACKGOUND OF THE INVENTION

Heterogeneous catalytic hydrogenation processes of various kinds are widely practised on a commercial scale. Typically such hydrogenation reactions are conducted at a pressure of from about 1 bar to about 300 bar and at a temperature in the range of from about 40° C. to about 350° C. Examples include hydrogenation of aldehydes to alcohols, of unsaturated hydrocarbons to saturated hydrocarbons, of acetylene-derived chemicals to saturated materials, of unsaturated fatty acids to saturated fatty acids, and of ketones to secondary alcohols. Thus cyclohexanol is produced commercially by catalytic hydrogenation of cyclohexanone, and isopropanol by catalytic hydrogenation of acetone. An example of hydrogenation of an unsaturated hydrocarbon is the production of cyclohexane from benzene. Typical catalysts for such hydrogenation reactions include Group VIII metal catalysts, such as nickel, palladium and platinum. This reaction is exothermic. The use of high temperatures is normally recommended so as to maximise conversion of benzene to cyclohexane, but isomerisation of cyclohexane to methyl cyclopentane, which is extremely difficult to separate from cyclohexane, can occur. Production of butane-1,4-diol by hydrogenation of but-2-yn-1,4-diol is an example of hydrogenation of an acetylene-derived chemical. A suitable catalyst for this reaction has been described as a granular nickel-copper-manganese on silica gel. The production of stearic acid by catalytic hydrogenation of the corresponding unsaturated acids, linoleic acid and linolenic acid, at a temperature of about 150° C. and at a pressure of about 14.75 bar to about 32 bar and using a nickel, cobalt, platinum, palladium, chromium or zinc catalyst, is an example of the hydrogenation of unsaturated fatty acids to yield saturated fatty acids.

An important route to $C_3$ and higher alkanols involves hydroformylation of alpha-olefins, such as ethylene, propylene, and butene-1, to yield the corresponding aldehyde having one more carbon atom than the starting olefin. Thus ethylene yields propionaldehyde and propylene yields a mixture of n- and iso-butyraldehydes (with the n-isomer usually predominating). These aldehydes yield the corresponding alkanols, e.g. n-propanol and n-butanol, upon catalytic hydrogenation. The important plasticiser alcohol, 2-ethylhexanol, is made by alkali-catalysed condensation of n-butyraldehyde to yield the unsaturated aldehyde, 2-ethyl-hex-2-enal, which is then hydrogenated to yield the desired 2-ethylhexanol. Although the preferred catalysts for such aldehyde hydrogenation reactions used to be Group VIII metal catalysts, such as nickel, palladium or platinum, the use of a solid catalyst comprising a reduced mixture of CuO and ZnO under vapour phase conditions has also been proposed (see EP-A No. 00 08 767 and U.S. Pat. No. 2,549,416). Molybdenum sulphide supported on an activated carbon carrier has also been suggested in GB-A No. 765,972. The hydrogenation of an aldehyde feed containing ring-type sulphur compounds using a reduced mixture of oxides or hydroxides of copper and zinc is described in U.S. Pat. No. 4,052,467. Copper chromite has also been used as an aldehyde hydrogenation catalyst.

Catalytic hydrogenation is in all the above cases a heterogeneous process. In designing a hydrogenation plant for, for example, production of n-butanol from n-butyraldehyde or of 2-ethylhexanol from 2-ethylhex-2-enal, a chemical engineer has to decide whether the process is to be operated as a liquid phase process or as a vapour phase process. The former offers the possibility of a compact plant but often high operating pressures have to be used as a rate determining factor is usually the low solubility of hydrogen in the organic liquid phase. This means that the costs of plant construction and operation are significant factors in the overall process economics. Vapour phase operation enables reaction pressures to be correspondingly lower but, as hydrogenation reactions are exothermic, temperature control problems may arise. If adiabatic reaction conditions are used, the rate of heat release may be so high that undesirable side reactions may occur and there is a considerable risk that the hydrogenation catalyst will become damaged through overheating. To moderate the temperature rise the vaporous stream may contain a considerable excess of hydrogen and/or an inert gas; however, this expedient increases the capacity of the gas recycle compressor. Another expedient that can be adopted to increase the heat capacity of the vaporous stream is to recycle some of the product alcohol and to vaporise this in the hydrogen-containing gas stream, together with the aldehyde to be hydrogenated. However, this means that a considerable excess of the hydrogen-containing gas must be used in order to prevent liquids from condensing on the catalyst, as well as being disadvantageous with respect to those reactions which are equilibrium controlled. Hence, although adiabatic reactors are generally relatively inexpensive as they are of simple construction, at least some of the capital and operating cost benefits are lost due to the necessarily increased size of the gas recycle compressor and of the whole plant due to the increased volume of gas recycle to be handled.

It is alternatively possible to operate a catalytic hydrogenation process, such as an aldehyde hydrogenation process in an externally cooled multitubular reactor. The capital cost of such a reactor is several times (often many times) higher than that of an adiabatic reactor and it is difficult and time-consuming to pack the multi-tubular reactor with catalyst. Moreover, in view of the many welds and the large surface areas exposed to the reactor cooling medium such as boiler feed water, there is a significant risk of tube weld failure occurring, which necessitates closing down the plant for repair.

A review of some of the factors involved in designing heterogeneous gas and vapour phase reaction systems appeared in "Chemical Engineering", July 1955, in an article entitled "Moving Bed - Processes . . . New Applications", at pages 198 to 206 (see in particular pages 204 and 205 thereof).

In U.S. Pat. No. 4,451,677 an aldehyde hydrogenation process is described in which a plurality of adiabatically operated catalytic hydrogenation stages connected in series is used. A part only of the aldehyde is fed, in the form of a vaporous first stream in admixture with excess hydrogen, to the first adiabatic stage. Substantially all of that aldehyde reacts in passage through that zone and the resulting substantially aldehyde-free product-containing stream is admixed with further aldehyde, or with an aldehyde/H₂ mixture that is richer in aldehyde than the first stream, and fed to a second adiabatic zone. Again, substantially all of the aldehyde reacts. If there are further stages, the aldehyde-free product-containing stream is mixed with further aldehyde or aldehyde/H₂ mixture and passed to the next adiabatic stage. According to U.S. Pat. No. 4,451,677 there occurs in each adiabatic stage substantially 100% hydrogenation of the aldehyde supplied to that stage.

Although this proposal offers significant capital and operating cost savings, compared with a plant of comparable capacity with conventional "pseudoisothermal" reactors, it is found that, with certain catalysts, a small but significant quantity of an ester byproduct is formed. This byproduct ester contains twice as many carbon atoms as the desired alkanol product and appears to be formed by a Tischenko reaction. Thus in hydrogenation of n-butyraldehyde, a significant byproduct is n-butyl n-butyrate:

2CH₃.CH₂.CH₂.CHO=CH₃.CH₂.CH₂.CO.O.CH₂.CH₂.CH₂.CH₃.

Similarly, when hydrogenating 2-ethylhex-2-enal, a byproduct may be the C₁₆ ester, 2-ethylhexyl 2-ethylhexanoate.

This byproduct ester can be recovered and subjected to hydrogenolysis to produce further product alcohol according to EP-A No. 0074193. However this represents an additional processing step which it would be desirable to obviate.

A further problem arises in hydrogenation of 2-ethylhex-2-enal in that the saturated aldehyde, 2-ethylhexanal, and the unsaturated alcohol, 2-ethylhex-2-enol, may also be formed as byproducts. In addition the crude 2-ethylhexanol may contain, in addition to the C₁₆ byproduct ester, 2-ethylhexyl-2-ethylhexanoate, also a minor amount of C₁₂ "heavies"; such C₁₂ "heavies" include, for example, trimeric aldehyde condensation products produced in the hydroformylation and aldolization steps. As these C₁₂ "heavies" co-distil with the C₁₆ byproduct ester, 2-ethylhexyl-2-ethylhexanoate, this complicates the treatment of the byproduct ester for the production of further 2-ethylhexanol by hydrogenolysis according to the teachings of EP-A No. 0074193. Moreover, as the boiling points of 2-ethylhexanal, of 2-ethylhex-2-enol, and of 2-ethylhex-2-enal are relatively close to that of 2-ethylhexanol, the separation of these four components is not easy to achieve in practice. The major use of 2-ethylhexanol is for production of the plasticiser, di-2-ethylhexyl phthalate. However, as the presence of even minor amounts of unsaturated materials in 2-ethylhexanol tends to impart a yellow colour to the resulting di-2-ethylhexyl phthalate, which renders it unacceptable for use as a plasticiser, the operator of a 2-ethylhexanol plant will usually seek to hydrogenate the intermediate aldehyde, 2-ethylhex-2-enal, as completely as possible so as to remove all unsaturated products, such as the intermediate, 2-ethylhex-2-enol, from the product 2-ethylhexanol. To this end the plant operator will often look to the use of relatively high reaction temperatures during the hydrogenation step. However, this will tend to increase the quantity of ester byproduct that is produced.

SUMMARY OF THE INVENTION

The present invention is concerned with seeking to overcome the problem of formation of by-products in hydrogenation reactions, for example formation of by-product ester, whilst reducing the quantity of chemically unsaturated material in the product stream to a minimum and retaining the benefits of operation under substantially adiabatic reaction conditions, particularly the capital cost benefits accruing from the use of low cost adiabatic reactors and the effective use of the heat of reaction.

According to one aspect of the present invention there is provided a continuous process for the catalytic hydrogenation of an unsaturated organic compound to a hydrogenation product thereof which comprises:

providing a catalytic hydrogenation zone comprising (i) a first catalytic stage, (ii) at least one intermediate stage, including a penultimate stage, and (iii) a final catalytic stage, each stage containing a charge of a hydrogenation catalyst and the stages being connected in series so that material from one stage is fed to the next stage in the series;

supplying to the first catalytic stage, at a first preselected rate and at a temperature at least as high as the threshold temperature for the hydrogenation reaction, a first vaporous feed mixture comprising excess hydrogen and the unsaturated organic compound;

allowing catalytic hydrogenation to occur substantially adiabatically in the first catalytic stage;

recovering from the, or from each, catalytic stage preceding the penultimate catalyst stage in the series a corresponding vaporous product mixture containing hydrogenation product and excess hydrogen;

vaporising in the, or in each, resulting vaporous product mixture a preselected amount of further unsaturated organic compound to form a corresponding vaporous feed stream for supply to the next catalytic stage in the series;

supplying to the, or to each, intermediate catalytic stage, at a corresponding preselected rate and at a temperature at least as high as the threshold temperature for the hydrogenation reaction, a corresponding intermediate vaporous feed stream comprising a mixture of further vaporous unsaturated organic compound and product mixture from the preceding catalytic stage of the series;

allowing hydrogenation to occur substantially adiabatically in the, or in each, intermediate catalytic stage;

controlling the rate of supply of, and the composition of, the corresponding intermediate vaporous feed stream fed to the penultimate catalytic stage in relation to the volume of catalyst therein so that, under the substantially adiabatic conditions prevailing in the penultimate catalytic stage, the product mixture recovered therefrom still contains a minor amount of chemically unsaturated material;

recovering from the penultimate catalytic stage a vaporous penultimate product mixture containing hydrogenation product, a minor amount of chemically unsaturated material and excess hydrogen;

cooling the vaporous penultimate product mixture;

supplying resulting cooled penultimate product mixture containing hydrogenation product, a minor amount of chemically unsaturated material and hydrogen to the final catalytic stage at a temperature at least as high as the threshold temperature for the hydrogenation reaction;

allowing hydrogenation of the minor amount of chemically unsaturated material in the penultimate product mixture to occur substantially to completion in the final catalytic stage; and recovering from the final catalytic stage a final product mixture that contains hydrogenation product and excess hydrogen and is substantially free from chemically unsaturated material.

The hydrogenation zone may include two or more intermediate catalytic stages. However in a preferred process the catalytic hydrogenation zone includes a single intermediate catalytic stage which forms the penultimate catalytic stage in the series, and the intermediate vaporous feed mixture to the intermediate catalytic stage comprises a mixture of further vaporous unsaturated organic compound and vaporous product mixture from the first catalytic stage.

The process of the invention involves use of at least three catalytic stages. A significant advantage of the process is that it offers the plant operator great flexibility of operation throughout the life of a catalyst charge, not only under design flow rate operating conditions but also under a wide variety of turndown conditions under which the rate of supply to the plant of the unsaturated organic compound to be hydrogenated is for any reason reduced from the flow rate at design capacity.

In the course of operation the activity of the charge of heterogeneous hydrogenation catalyst in any hydrogenation plant will inevitably decline with time. In a single stage hydrogenation plant the operator can compensate for such decline in catalyst activity by raising the operating temperatures in the plant. However, although this expedient helps to maintain the throughput of material, it also results in an increase in the "hot spot" temperature and hence in an increased risk of byproduct formation. Although some improvement in plant operation compared with a single stage hydrogenation plant could be obtained by utilising two catalytic stages, in the first of which the bulk of the unsaturated organic compound, for example about 95% thereof, is hydrogenated under adiabatic hydrogenation conditions, whilst the second stage is used to hydrogenate the remaining 5% or so of chemically unsaturated material in the cooled intermediate product from the first catalytic stage, such an arrangement would still not permit the operator to compensate for decline in catalyst activity without raising the inlet temperature to the first catalytic stage, nor would it allow him to operate the plant optionally under turndown conditions.

In the process of the invention not only can the plant operator compensate for a loss of catalyst activity without having to raise the inlet temperature but also he can operate efficiently under a wide variety of turndown conditions. In each case this can be done, without having to increase operating tempratures significantly, by adjusting the relative rates of supply of the unsaturated organic compound used as starting material to the first catalytic stage, on the one hand, and to the or each intermediate catalytic stage, on the other hand, in order to compensate for loss of catalyst activity and/or for a reduction in rate of supply of starting material to the plant.

The process may further include the step of controlling the rate of supply of, and the composition of, the feed mixture to the, or to each, catalytic stage preceding the penultimate stage in the series in relation to the volume of the catalyst therein so that, under the substantially adiabatic conditions prevailing therein, the product mixture recovered therefrom still contains a minor amount of chemically unsaturated material. Such chemically unsaturated material may comprise, depending upon the nature of the hydrogenation reaction concerned, the unsaturated compound used as starting material, one or more chemically unsaturated intermediate products, or a mixture thereof.

In order to obviate any risk of condensation of condensible components on the catalyst it is preferred that the entry temperature to the first catalytic stage and the entry temperature to the, or to each, intermediate catalytic stage is, in each case, at least about 5° C. to about 15° C. above the dew point of the corresponding vaporous feed mixture.

Although the final catalytic stage can be operated under liquid phase conditions, it will usually be preferred for the cooled penultimate product mixture to be supplied in vaporous form to the final catalytic stage. In this case the entry temperature to the final catalytic stage is also at least about 5° C. to about 15° C. above the dew point of the mixture.

Hydrogenation of the minor amount of chemically unsaturated material in the penultimate product mixture can be allowed to occur substantially adiabatically in the final catalytic stage. When the final catalytic stage is operated under vapour phase conditions recovery of hydrogenation product from the final product mixture is usually conveniently effected by cooling so as to condense the hydrogenation product therefrom.

It can also be provided that part of the hydrogenated product recovered from the final product mixture is recycled for vaporisation in at least one of the vaporous streams supplied to the first catalytic stage or to the, or to one of the, intermediate catalytic stages.

In a particularly preferred mode of operation the step of controlling the rate of supply of, and the composition of, the corresponding intermediate vaporous stream fed to the penultimate catalytic stage includes the steps of monitoring the temperature rise across the final catalytic stage and adjusting the preselected amount of unsaturated organic compound that is vaporised in the vaporous product mixture from the antepenultimate catalytic stage so that the temperature rise across the final catalytic stage lies within a predetermined range.

If the overall rate of supply of unsaturated organic compound to the catalytic hydrogenation zone is, for any reason, reduced to a rate that is less than the design capacity of the plant, then it is preferred that any reduction in the rate of supply of unsaturated organic compound to the penultimate catalytic stage from the respective flow rate thereto at design capacity is proportionately significantly less than any corresponding reduction in the rate of supply of unsaturated organic compound to any preceding catalytic stage from the respective flow rate thereto at design capacity.

The invention further provides a continuous process for the catalytic hydrogenation of an unsaturated organic compound to a hydrogenation product thereof which comprises:

providing a catalytic hydrogenation zone comprising first, second and third catalytic stages connected in series, each containing a charge of a hydrogenation catalyst;

supplying to the first catalytic stage, at a first preselected rate and at a temperature at least as high as the threshold temperature for the hydrogenation reaction, a first vaporous feed stream comprising excess hydrogen and the unsaturated organic compound;

allowing catalytic hydrogenation to occur substantially adiabatically in the first catalytic stage;

recovering from the first catalytic stage a vaporous first product stream containing hydrogenation product and excess hydrogen;

vaporising in the first product stream a preselected amount of further unsaturated organic compound to form a second vaporous feed stream;

supplying the second vaporous feed stream to the second catalytic stage at a second preselected rate and at a temperature at least as high as the threshold temperature for the hydrogenation reaction, the preselected amount being so chosen in relation to the volume of the catalyst charge in the second catalytic stage and to the second preselected rate that, upon allowing hydrogenation to occur substantially adiabatically in the second catalytic stage, the product mixture recovered therefrom still contains a minor amount of chemically unsaturated material;

allowing hydrogenation to occur substantially adiabatically in the second catalytic stage;

recovering from the second catalytic stage a vaporous second product mixture containing hydrogenation product, a minor amount of chemically unsaturated material and excess hydrogen;

cooling the vaporous second product mixture;

supplying a third feed stream comprising cooled second product mixture to the third catalytic stage at a temperature at least as high as the threshold temperature for the hydrogenation reaction;

allowing hydrogenation of the minor amount of chemically unsaturated material in the second product mixture to occur substantially to completion in the third catalytic stage; and recovering from the third catalytic stage a third product mixture that contains hydrogenation product and excess hydrogen and that is substantially free from chemically unsaturated material.

The process of the invention is not specific to any particular hydrogenation reaction or to any particular catalyst composition. It is, however, particularly suitable for use in hydrogenation reactions in which by-products are likely to be formed in the event that the reaction mixture is exposed to the catalyst for a significant length of time at elevated temperature. Thus the process of the invention is applicable to a wide variety of hydrogenation reactions so long as the unsaturated organic compound to be hydrogenated can be vaporised. For example, it can be applied to the hydrogenation of unsaturated hydrocarbons to saturated hydrocarbons. Typical of such a reaction is the production of cyclohexane from benzene. This hydrogenation can be carried out according to the invention using, in each catalytic stage, a nickel, palladium or platinum catalyst, a temperature of from about 100° C. to about 350° C., and a pressure of from about 5 bar to about 30 bar. Production of secondary alcohols by reduction of ketones is another appropriate hydrogenation reaction to which the invention can be applied. Examples of such reactions include production production of iso-propanol from acetone and of cyclohexanol from cyclohexanone.

Another example of a hydrogenation reaction to which the present invention can be applied is the production of butane-1,4-diol by hydrogenation of but-2-yn-1,4-diol. This can be carried out using a catalyst which is a granular nickel-copper-manganese on silica gel at a pressure of from about 200 bar to about 300 bar in each catalytic stage. A typical inlet temperature is about 40° C., when the catalyst is fresh, and a typical exit temperature is about 130° C.

A further example of a hydrogenation reaction to which the process of the invention can be applied is the production of stearic acid by hydrogenation of linoleic acid, of linolenic acid, or of a mixture thereof. This can be carried out using a nickel, cobalt, platinum, palladium, chromium or zinc catalyst at a pressure of from about 14.75 bar to about 32 bar in each catalytic stage and an inlet temperature of about 150° C.

A particularly preferred type of hydrogenation reaction is the production of alcohols from aldehydes. Such aldehydes generally contain from 2 to about 20 carbon atoms and may include one or more unsaturated carbon-carbon bonds. Thus as used herein the term "aldehyde" includes both saturated aldehydes (that is to say aldehydes in which the only hydrogenatable group is an aldehyde group —CHO) and unsaturated aldehydes (that is to say aldehydes which contain other hydrogenatable groups besides any aldehyde group —CHO present). Typical aldehydes include acetaldehyde, propionaldehyde, n- and iso-butyraldehydes, n-pentanal, 2-methylbutanal, 2-ethylhex-2-enal, 2-ethylhexanal, $C_{10}$-"OXO"-aldehydes (e.g. 2-propylhept-2-enal), crotonaldehyde and furfural, as well as mixtures of two or more thereof. Examples of aldehyde hydrogenation reactions are the production of propanol from propionaldehyde, of n-butanol from n-butyraldehyde, and of 2-ethylhexanol from 2-ethylhex-2-enal. In such aldehyde hydrogenation reactions there can be used any of the conventionally used metal catalysts, such as Ni, Pd or Pt, or copper chromite. In a particularly preferred process the aldehyde hydrogenation catalyst is a reduced mixture of CuO and ZnO of the type disclosed in EP-A No. 00 08 767 and U.S. Pat. No. 2,549,416. According to EP-A No. 00 08 767 catalysts of this type under appropriately selected reaction conditions give rise to negligible formation of byproducts, such as ethers and hydrocarbons, and also to small amounts only of "heavies" formation (such as esters) when aldehydes are hydrogenated.

Other aldehyde hydrogenation catalysts include cobalt compounds; nickel compounds which may contain small amounts of chromium or another promoter; mixtures of copper and nickel and/or chromium; and other Group VIII metal catalysts, such at Pt, Pd, Rh and mixtures thereof, on supports, such as carbon, silica, alumina and silica-alumina. The nickel compounds are generally deposited on support materials such as alumina or kieselguhr.

An important feature of the process of the invention is that hydrogenation of the aldehyde, or other unsaturated organic compound, need not be complete in the penultimate catalytic stage thus reducing the exposure of the reaction products to the catalyst at high temperature to a minimum. This avoids significant formation of byproducts, such as esters if aldehydes are the feed materials, which results from prolonged exposure of the organic compounds to the catalyst at high temperature in any attempt to obtain a maximum amount of product hydrogenation. Hence the product mixture from the penultimate catalytic stage still contains a minor amount of chemically unsaturated material. Such chemically unsaturated material may comprise the unsaturated organic compound itself or, if the hydrogenation reaction may give rise to one or more unsaturated intermediates or byproducts, a material selected from at least one such intermediate or byproduct, the unsaturated organic compound, and a mixture thereof. Preferably the feed rate of the material to be hydrogenated to the penultimate stage is controlled so that, under the substantially adiabatic conditions prevailing in the penultimate stage, from about 50% to about 99% of the chemically unsaturated material supplied to that stage is hydrogenated. More usually the degree of hydrogenation in passage through the penultimate stage will be from about 75% to about 98%, e.g. about 85% to about 96%. If the process is operated so that the degree of hydrogenation in one or more stages preceding the penultimate catalytic stage is also less than 100%, then these stages can also be operated so as to result in a degree of hydrogenation within the above ranges in each case.

Taking, for example, the hydrogenation of aldehydes, the chemically unsaturated material from the penultimate catalytic stage may be the aldehyde itself when the unsaturated organic compound is an alkanal, such as propionaldehyde or n-butyraldehyde. However, when the aldehyde contains further unsaturation, in addition to the —CHO group, the chemically unsaturated material may comprise a material selected from the aldehyde and from mixtures thereof with partially hydrogenated products of the unsaturated aldehyde. For example, when hydrogenating 2-ethylhex-2-enal, the chemically unsaturated material may comprise a material selected from 2-ethylhex-2-enal, 2-ethylhex-2-enol, 2-ethylhexanal and a mixture of two or more thereof.

The process of the invention may be operated with a substantially pure hydrogen gas or with a hydrogen containing gas which may be made up in part of recycled gas. When using such recycled gas the hydrogen-containing gas preferably contains at least about 20 mole %, and more preferably at least about 50 mole %, hydrogen with the balance comprising gaseous inerts, such as nitrogen, methane, other low molecular weight hydrocarbons, one or more carbon oxides (i.e. CO and/or $CO_2$), and one or more inert gases such as argon. The presence in the gas of methane and/or other low molecular weight hydrocarbons (e.g. ethane, propane, and/or n- or iso-butane), and/or carbon oxides is beneficial in that the heat capacity of the gas mixture is thereby increased, thus enabling the volume of the circulating gas to be correspondingly reduced. As, however, a reduction in volume of the circulating gas results in a reduction in the amount of aldehyde and/or recycled alcohol that can be vaporised in the gas stream, the level of inerts will not usually exceed about 80% by volume of the circulating gas and more normally is less than about 50% by volume. A gas purge stream may be taken in order to control the level of inerts in the circulating gas.

The gas used as make up hydrogen-containing gas preferably comprises at least about 90 mole %, more preferably at least about 95 mole %, hydrogen with the balance comprising gaseous inerts.

Part of the alcohol (or other hydrogenated product) recovered in the final product stream can optionally be recycled for vaporisation in the vaporous feed stream supplied to the penultimate catalytic stage and/or to the, or to one of the, stages preceding the penultimate catalytic stage for the purpose of increasing the heat capacity of the corresponding vaporous feed stream. Usually the amount of hydrogenated product that is recycled will not exceed about 25% of the total product recovered from the final product stream. Such recycled hydrogenated material may comprise impure material as recovered from the final product mixture or may comprise purified product from a downstream refining zone, for example from a distillation zone.

In some cases the final product mixture may include a small amount, which is usually no more than a trace amount, of chemically unsaturated material, due to the hydrogenation reaction being equilibrium limited. In this case such small amount of chemically unsaturated material can be separated from the product in the refining zone and recycled, possibly in admixture with recycled hydrogenation product, for vaporisation in the vaporous feed stream to one of the catalytic stages preceding the final catalytic stage. This expedient can be adopted if, for example, the final product mixture for any reason contains a significant, but small amount of chemically unsaturated material, as may occur under certain circumstances at start up of the plant or if the operating conditions are for any reason allowed to deviate from optimum operating conditions.

In the process of the invention further aldehyde or other unsaturated organic compound is vaporised in the product stream from the or each catalytic stage preceding the penultimate catalytic stage. In addition, further hydrogen-containing gas can be added to the mixture prior to entry to the next catalytic stage.

Also provided in accordance with the invention is a continuous process for the catalytic hydrogenation of an aldehyde to a corresponding alcohol which comprises:

providing a catalytic hydrogenation zone comprising n catalytic stages in series, where n is an integer of at least 3, each catalytic stage containing a charge of a solid hydrogenation catalyst effective for catalytic hydrogenation of aldehydes;

supplying to the first catalytic stage a first vaporous mixture comprising excess hydrogen and the aldehyde at a first temperature which is equal to, or is in excess of, the threshold temperature for the hydrogenation reaction;

allowing catalytic hydrogenation to occur substantially adiabatically in each catalytic stage up to and including the $(n-1)$th catalytic stage, thereby to effect hydrogenation to corresponding alcohol of aldehyde supplied to that stage;

vaporising further aldehyde in the vaporous product mixture from the, or from each, mth catalytic stage in the series, where m is an integer equal to or less than $(n-2)$, to form a corresponding vaporous feed mixture for supply to the corresponding $(m+1)$th catalytic stage in the series;

supplying resulting vaporous feed mixture to the corresponding $(m+1)$th catalytic stage at a temperature which is equal to, or is in excess of, the threshold temperature for the hydrogenation reaction;

controlling the rate of supply of, and the composition of, the corresponding vaporous feed stream to the $(n-1)$th catalytic stage in relation to the volume of catalyst therein so that, under the substantially adiabatic conditions prevailing in the $(n-1)$th catalytic stage, the product mixture recovered therefrom still contains a minor amount of chemically unsaturated material;

recovering from the $(n-1)$th catalytic stage a vaporous product mixture containing product alcohol, a minor amount of chemically unsaturated material, and excess hydrogen;

cooling the product mixture from the $(n-1)$th catalytic stage;

supplying cooled product mixture from the $(n-1)$th catalytic stage to the nth catalytic stage at a temperature which is equal to, or in excess of, the threshold temperature for the hydrogenation reaction;

allowing hydrogenation to proceed substantially to completion in the nth catalytic stage; and recovering from the nth catalytic stage a final vaporous product mixture that contains the corresponding product alcohol and that is substantially free from chemically unsaturated material.

BRIEF DESCRIPTION OF THE DRAWINGS

In order that the invention may be clearly understood and readily carried into effect a preferred embodiment thereof will now be described, by way of example only, with reference to the accompanying drawings, wherein.

Figure 1:
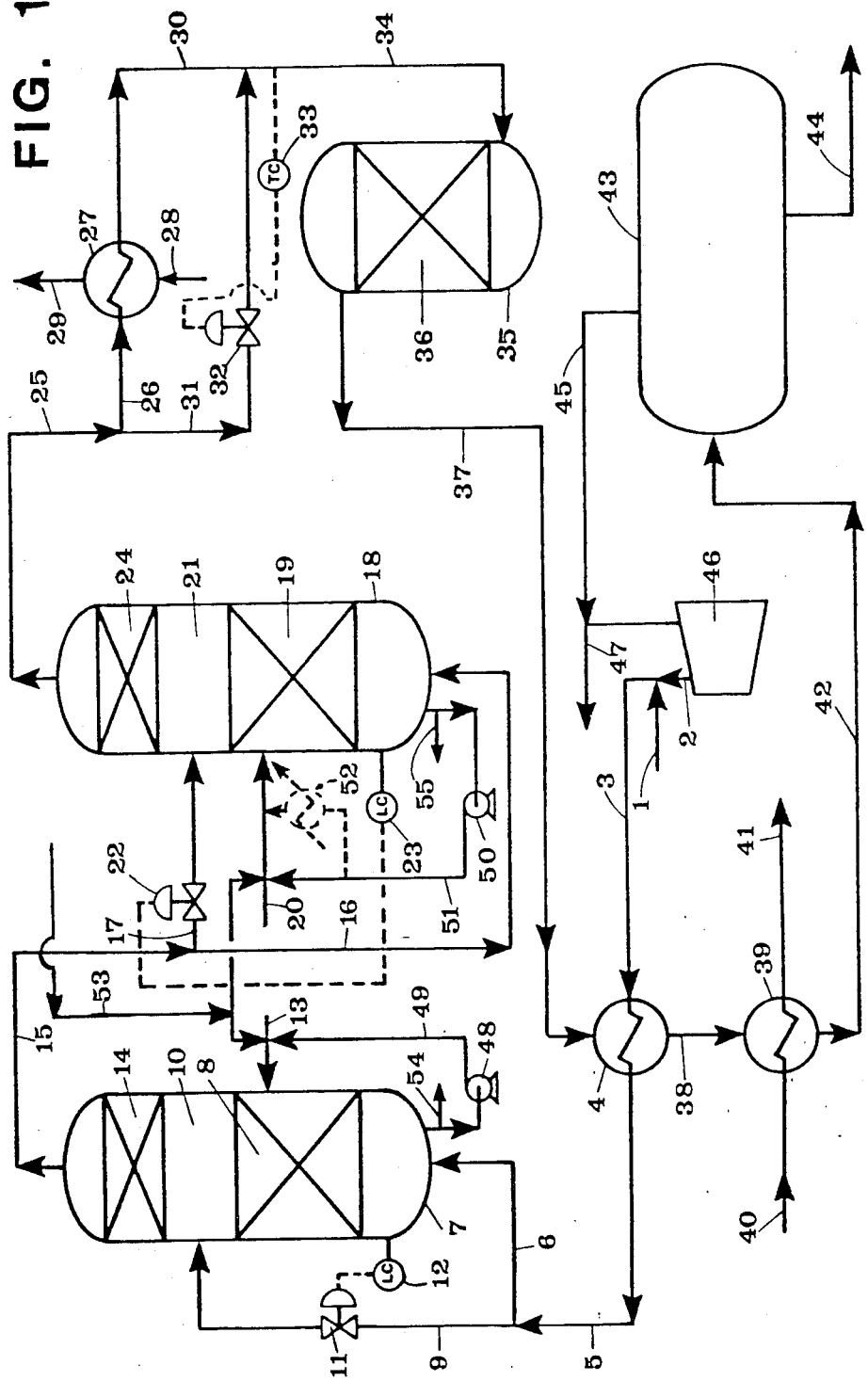
FIG. 1 is a simplified flow diagram of an aldehyde hydrogenation plant constructed in accordance with the invention.
Figure 7:
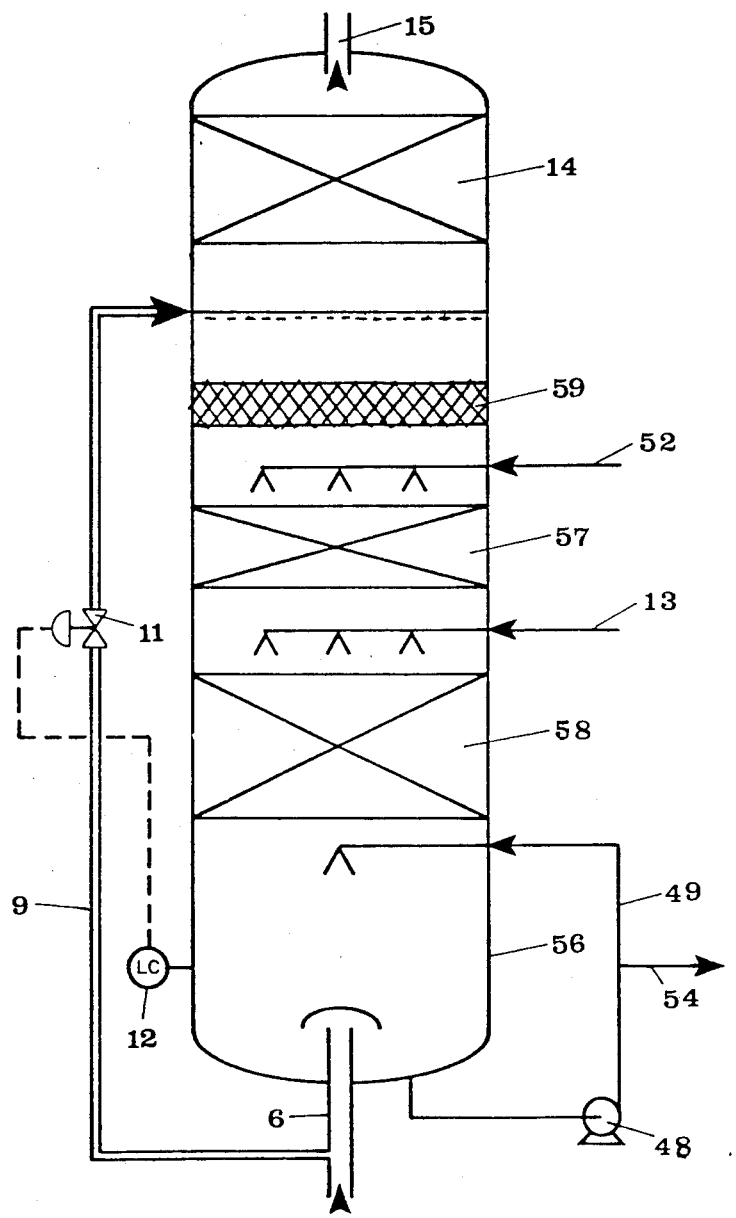
FIG. 7 is a diagrammatic view of an alternative design of combined vaporiser and reactor vessel for use in the plant of FIG. 1.

It will be understood by those skilled in the art that FIGS. 1, 7 and 8 are diagrammatic and that further items of equipment such as temperature and pressure sensors, pressure relief valves, control valves, level controllers and the like would additionally be required in a commerical plant. The provision of such ancillary items of equipment forms no part of the present invention and would be in accordance with conventional chemical engineering practice. Moreover it is not intended that the scope of the invention should be limited in any way by the precise methods of cooling, heating and vaporising the various process streams, or by the arrangement of coolers, heaters, heat exchangers, and vaporising apparatus provided therefor, illustrated in any of FIGS. 1, 7 and 8; any other suitable arrangement of equipment fulfilling the requirements of the invention may be used in place of the illustrated equipment in accordance with conventional chemical engineering techniques.

DESCRIPTION OF THE PREFERRED EMBODIMENTS

Referring to the drawings, and to FIG. 1 in particular, make up hydrogen is supplied to the illustrated multi-stage hydrogenation plant in line 1 and is admixed with recycled gas in line 2. The combined gas flow is passed on in line 3, at a pressure of 12.1 bar, to a heat exchanger 4 in which it undergoes indirect heat exchange with the product stream from the final catalytic hydrogenation stage. The heated gas, now at a temperature of 135° C., flows on in line 5; part is supplied in line 6 to the bottom of a vessel 7, the lower part of which is provided with a packed volume 8 forming a vaporisation zone, whilst the remainder is fed in bypass line 9 to an upper part 10 of vessel 7. The relative proportions of hot gas that flow in lines 6 and 9 are controlled by means of a valve 11 in line 9, which is itself controlled by a liquid level controller 12 that senses the liquid level in the lower part of vessel 7.

Ethyl propyl acrolein (i.e. 2-ethylhex-2-enal) is supplied at a controlled rate in line 13 to vaporisation zone 8 and is vaporised therein by contact with the ascending hot gas. The resulting vaporous mixture flows into upper part 10 of vessel 7 and is mixed therein with further hydrogen-containing gas supplied in bypass line 9 to yield a first vaporous mixture, containing 2-ethylhex-2-enal and excess hydrogen at an aldehyde:H$_2$ molar ratio of about 1:50, which is about 10° C. above its dew point. Typically the ratio of the gas flows in lines 6 and 9 is about 75:25 by volume. This first vaporous mixture then flows into a first catalytic stage formed by a bed of catalyst 14 positioned at the upper end of vessel 7. The catalyst is a reduced mixture of CuO and ZnO of the type recommended in EP-A No. 00 08 767. The aldehyde, 2-ethylhex-2-enal, undergoes hydrogenation under substantially adiabatic conditions in passage through catalyst bed 14 according to the following equation:

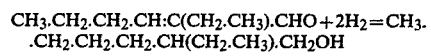

$$CH_3.CH_2.CH_2.CH:C(CH_2.CH_3).CHO + 2H_2 = CH_3.CH_2.CH_2.CH_2.CH(CH_2.CH_3).CH_2OH$$

However, the rate of supply of 2-ethylhex-2-enal in line 13 is limited so that, in passage through catalyst bed 14, only about 95% of the aldehyde undergoes complete hydrogenation to 2-ethylhexanol.

There exits from vessel 7 in line 15 a vaporous first product mixture at a temperature of 185° C. This contains 2-ethylhexanol, 2-ethylhexanal and hydrogen in a molar rate of 19:1:960. The bulk of this mixture, typically about 65% by volume, passes on in line 16 whilst the remainder passes into bypass line 17. Line 16 leads to the bottom of a second vessel 18, the bottom end of which includes a packed vaporisation zone 19. Further 2-ethylhex-2-enal is fed in line 20 to vaporisation zone 19 and is vaporised in the upflowing stream. The resulting vaporous mixture flows upwards into an empty zone 21 and is mixed therein with the by-passed first product mixture from line 17. In this way a second vaporous feed mixture at a temperature of 160° C., which is 10° C. above its dew point, is formed. The proportions of material flowing in lines 16 and 17 are controlled by a valve 22 in dependence on the liquid level in the case of vessel 18 by means of a suitable liquid level controller 23. The second vaporous feed mixture passes upwardly through a second bed 24 of the catalyst at the top end of vessel 18. The rate of supply of 2-ethylhex-2-enal is so selected in relation to the volume of catalyst in bed 24 and to the flow rate in line 15 that not all of the hydrogenatable material undergoes hydrogenation in passage through bed 24. The aldehyde:H$_2$ molar ratio in the second vaporous feed mixture entering catalyst bed 24 is about 1:32.9.

A second product mixture containing 2-ethylhexanol, 2-ethylhexanal and excess hydrogen in a molar ratio of 24:1:450 is recovered from vessel 18 at a temperature of 240° C. in line 25. This second product mixture also contains traces of 2-ethylhex-2-enol, as well as traces of unreacted 2-ethylhex-2-enal. Part of the second product mixture flows in line 26 through boiler 27, which is supplied with boiler feed water in line 28 and yields steam in line 29, into line 30, whilst the remainder flows in bypass line 31 and is admixed, downstream from boiler 27, with the stream in line 30. Valve 32 is used to control the proportions of material flowing in lines 26 and 30, this valve being controlled in turn by a temperature controller 33 connected to a temperature sensor in line 34 which receives the combined flows from lines 30 and 31. Valve 32 is arranged to provide for the temperature of the material in line 34 to be 160° C., which is about 10° C. above the dew point of the mixture. This mixture is then fed to vessel 35 which contains a third catalyst bed 36. Again, the catalyst is a reduced CuO-ZnO catalyst of the type recommended in EP-A No. 00 08 767. In passage through bed 36 the residual 2-ethylhexanal and other chemically unsaturated materials are converted to 2-ethylhexanol. This is accompanied by a temperature rise of about 5° C. Hence the exit temperature of the final product mixture exiting vessel 35 in line 37 is 165° C. This mixture passes through heat exchanger 4, in which it gives up heat to the hydrogen-containing gas in line 3, and passes on in line 38 to condenser 39 which is supplied with cooling water in line 40. Reference numeral 41 indicates the cooling water exit line. The resulting mixture of condensate and gas passes on in line 42 to a catchpot 43 from which crude 2-ethylhexanol is withdrawn in line 44. Unreacted hydrogen is recycled in line 45 to gas recycle compressor 46 in which it is recompressed for supply to line 2. A purge gas stream is taken in line 47 in order to control the level of inerts (e.g. $N_2$, $CH_4$, A, etc) in the circulating gas to about 50 mole %.

Unvaporised aldehyde from the bottom of vessel 7 is recycled for vaporisation in zone 8 by means of pump 48 and line 49. Pump 50 and line 51 are similarly provided for recycling unvaporised aldehyde from the bottom of vessel 18 to vaporisation zone 19. A steam heated preheater 52 can be included in the aldehyde recycle loop for vessel 18 for a purpose which will be further explained below. A recycle line 53 is provided for recycling impure 2-ethylhexanol for admixture with feed aldehyde in lines 13 and/or 20. Such impure 2-ethylhexanol may comprise a 2-ethylhexanol fraction that is enriched with unsaturated $C_8$ compounds recovered in a downstream refining section (not shown in FIG. 1) to which the crude 2-ethylhexanol in line 44 is fed.

Typically the recycle rate of 2-ethylhexanol corresponds to about 10% to about 15% of the total alcohol produced. Lines 54 and 55 are purge lines provided to prevent build up of "heavies" in the bottom of vessels 7 and 18 respectively.

The crude 2-ethylhexanol product in line 44 is substantially free from byproduct ester, i.e. 2-ethylhexyl 2-ethylhexanoate, as well as from unreacted 2-ethylhex-2-enal and from the saturated aldehyde, 2-ethylhexanal. It can be further purified, if desired by conventional distillation techniques. Typically the concentration of 2-ethylhexanal in this crude 2-ethylhexanol stream in line 4 is no more than about 0.75% by weight, while the concentration of the $C_{16}$ ester, 2-ethylhexyl 2-ethylhexanoate, is no more than about 0.20% by weight.

Figure 2:
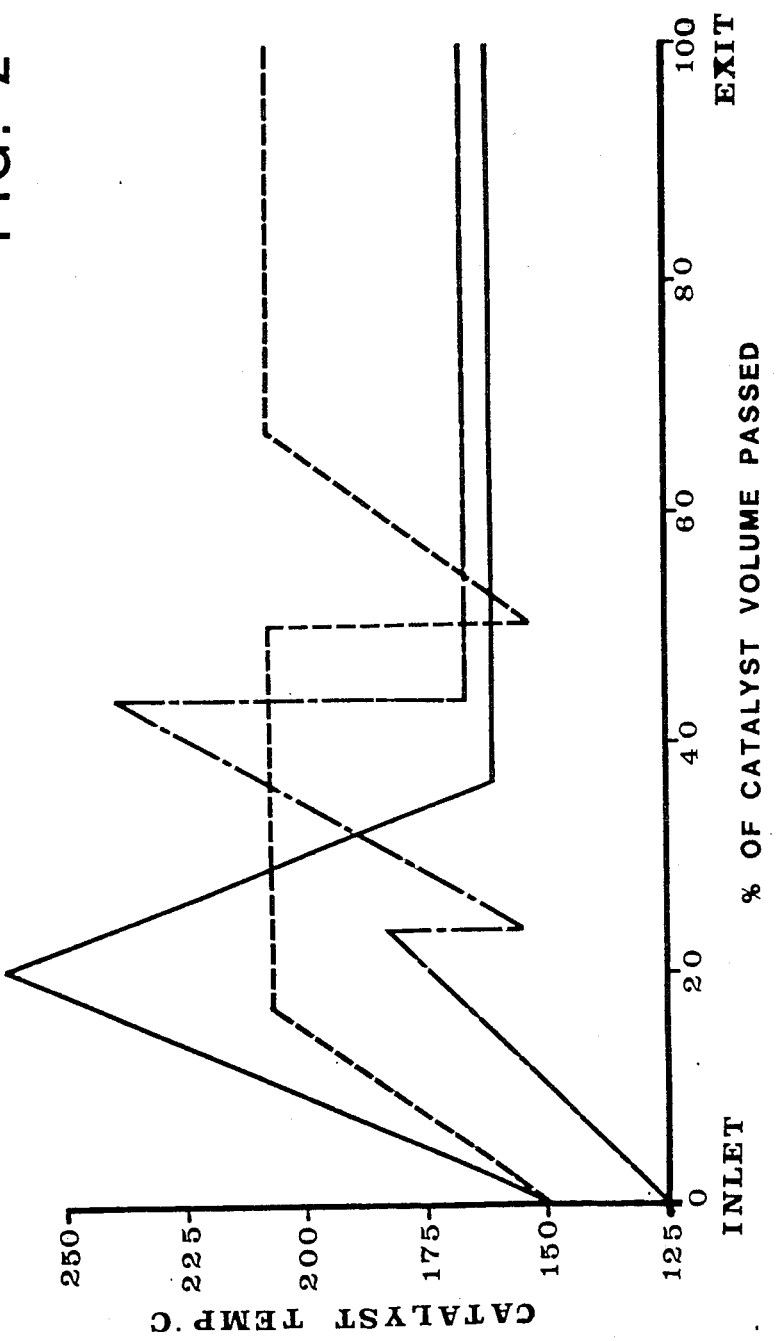
FIG. 2 is a graph of temperature against time of contact with the catalyst for various designs of aldehyde hydrogenation plant.

FIG. 2 is a graph in which catalyst temperature is plotted against percentage of catalyst volume passed for three different designs of 2-ethylhex-2-enal hydrogenation plant. This shows diagrammatically a typical temperature profile for a conventional cooled multi-tubular reactor operating with a coolant temperature of 160° C.; this is the curve shown as a continuous line. In this design the entry temperature to the reactor is 150° C. and a peak temperature of 260° C. is reached about 20% of the way along the reactor from its inlet end. The reaction mixture exiting the reactor is substantially aldehyde free, so that hydrogenation proceeds substantially to completion in passage through the reactor. The curve shown with a broken line is the temperature profile for a two reactor system, each operating adiabatically, as described in U.S. Pat. No. 4,451,677. In this case essentially all aldehyde supplied to each adiabatic reactor is hydrogenated in passage therethrough so that the reaction mixture exiting each reactor is aldehyde free. Again the inlet temperature is 150° C., but the peak temperature in each bed is lower i.e. 210° C. In this case the peak temperature occurs about one third of the way along each reactor from its inlet end. However, the "soak" time at the peak temperature is appreciable in each reactor. Our experimental work has shown that the quantity of byproduct ester (e.g. 2-ethylhexyl 2-ethylhexanoate, when the aldehyde undergoing hydrogenation is 2-ethylhex-2-enal) increases with increasing temperature and with time of contact with the catalyst at elevated temperatures; hence a disadvantage of the multistage adiabatic process of U.S. Pat. No. 4,451,677 is that, although that process offers significant capital and operating cost savings compared with the use of a conventional cooled multi-tubular reactor, the amount of such byproduct ester formed is correspondingly higher for the multi-stage adiabatic system than for the conventional cooled multi-tubular reactor. In the case of the cooled multi-tubular reactor, although the peak temperature achieved is somewhat higher than in the multi-stage adiabatic system of U.S. Pat. No. 4,451,677, the dwell time at peak temperature in contact with the catalyst is much shorter than for the multi-stage adiabatic process.

The third graph of FIG. 2, in which the temperature profile curve is shown by a dot-dash broken line illustrates a typical temperature profile for the plant of FIG. 1 operating at design capacity, but with only 95% of the 2-ethylhex-2-enal supplied to the first two stages undergoing reaction, so that the reaction mixture exiting the first and second stages contains free aldehyde in each case. The entry temperature to the first reactor is 125° C. and the peak temperature in the first reactor is 185° C., at the exit end of the first reactor. After further aldehyde has been vaporised in the reaction mixture from the first adiabatic reactor, the entry temperature to the second adiabatic reactor is 160° C. Again the peak temperature is at the exit end of the second adiabatic reactor but this time it is 240° C. Hydrogenation is again only about 95% complete at the exit end of the second adiabatic reactor. The incompletely reacted mixture from the second reactor is cooled to 160° C. and fed to the third reactor. Although the dwell time in the third reactor is quite long, the temperature rise is quite small, i.e. about 5° C. at most. Hence, although a completely reacted, aldehyde free reaction products stream is recovered at the downstream end of the third reactor, this stream has only been exposed to temperatures in excess of 200° C. for a brief period. In contrast the dwell time above 200° C. in the conventional cooled multitubular reactor is about twice as long, and in the multistage adiabatic process of U.S. Pat. No. 4,451,677 the dwell time above 200° C. is about 7.33 times as long. Thus the ester byproduct content of the reaction product stream from the third reactor used in the process of the present invention is significantly lower than that of the reaction product stream obtained in either of the two prior art proposals.

The plant of FIG. 1 was described above as operating at design throughput. In practice gradual decline of catalyst activity will occur with passage of time so that, if the operating conditions are not changed, the alcohol output of the plant will also gradually decline and the rate of supply of aldehyde via the lines 13 and 20 will also have to be correspondingly reduced.

One way of compensating for decline in catalyst activity is to increase the operating temperatures. For example, an increase in operating temperature of 10° C. will raise the activity of the hydrogenation catalyst by about 10%. However, any increase in operating temperature will tend rapidly to increase the amount of ester byproduct formed.

Figure 3:
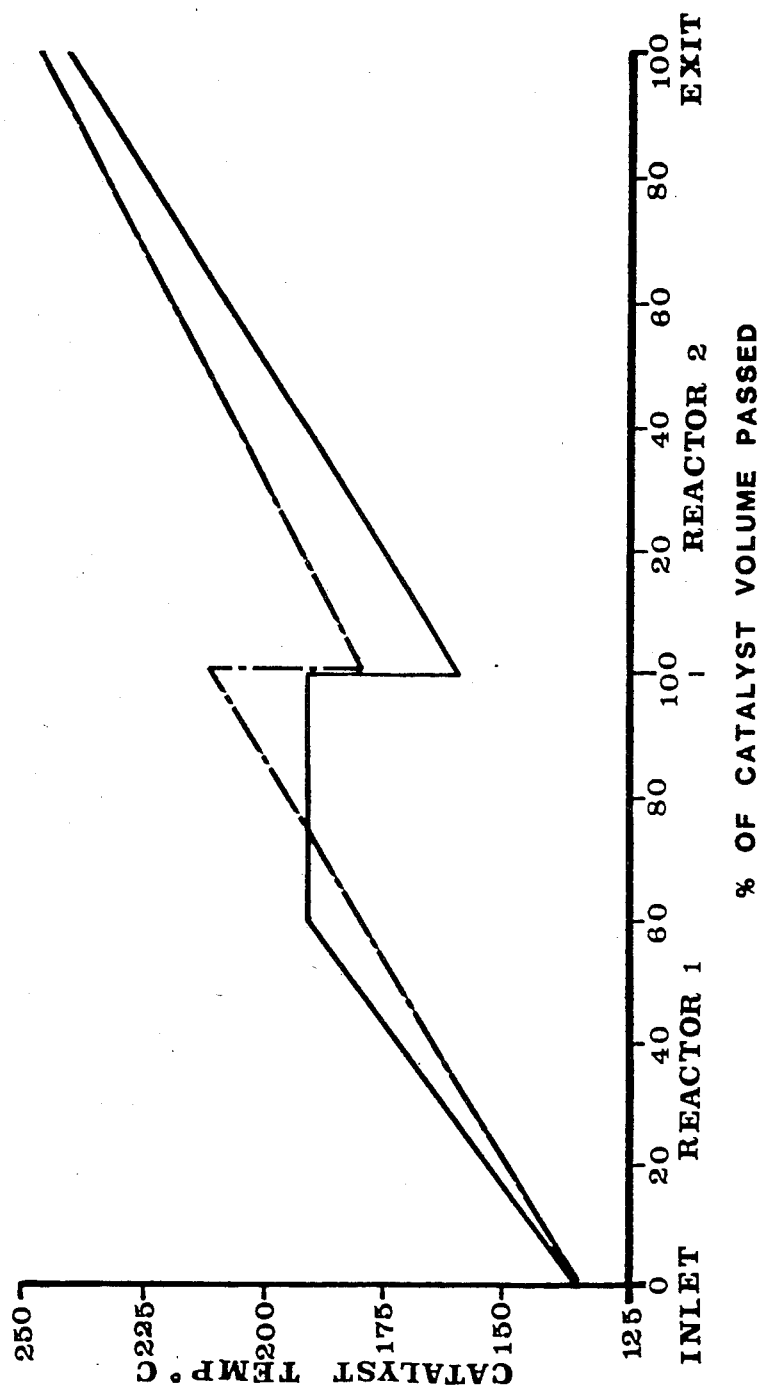
FIGS. 3 to 6 are graphs illustrating operation of the plant of FIG. 1 under a variety of operating conditions.

A plant designer can allow for a gradual decay in activity of the hydrogenation catalyst in the basic design of the plant, without having to increase operating temperatures, and permit efficient operation under a wide variety of turndown conditions, such as may prevail, for example when demand for product alcohol is low or when supply of aldehyde intermediate is for some reason interrupted. To achieve this end, having decided on the design capacity of the plant, a volume of hydrogenation catalyst is chosen that will suffice for hydrogenation of (say) 130% of the design throughput of aldehyde. This is divided between the three catalyst beds 14, 24 and 36. Conveniently vessels 7 and 18 are identical and the beds 4 and 24 are also identical in volume. Under design operating conditions a major proportion, e.g. 62.5%, of the aldehyde is fed through line 20 at the start of catalyst life, whilst the remaining minor portion, e.g. 37.5%, is fed through line 13. Under such conditions there will be excess catalyst capacity in bed 14 so that hydrogenation of the aldehyde supplied in line 13, amounting to 37.5% of the total aldehyde to be reacted, will be substantially complete in catalyst bed 14. Thus the exit stream in line 15 is essentially aldehyde free. Although this means that the "hot spot" will occur only part way up the bed 14, and so the dwell time of the product mixture in contact with the catalyst at elevated temperature is appreciable, the "hot spot" temperature in catalyst bed 14 is relatively low, e.g. about 190° C., because the quantity of aldehyde being hydrogenated in bed 14 is relatively low and the hydrogen:aldehyde molar ratio is high, e.g. about 60:1. Hence little byproduct ester is produced in passage through bed 14. Vaporisation of the remaining 62.5% of the aldehyde in vaporisation zone 19 results in cooling of the vaporous stream from bed 14 and in an inlet temperature to catalyst bed 24 of 165° C. The "hot spot" temperature at the exit end of catalyst bed 24 is 240° C. As the "hot spot" is at the exit end of bed 24, the dwell time of the mixture at such "hot spot" temperature is negligible. Hence little or no ester byproduct will be formed in passage through bed 24. As the catalyst activity declines, a greater proportion of the aldehyde is supplied via line 13. At the end of catalyst life, when the original activity has declined to about 75% of its original activity, a circumstance that may take a very considerable time, perhaps several years, to come to pass, 50% of the aldehyde is supplied in each of lines 13 and 20. In this case hydrogenation is not fully complete (i.e. perhaps about 90% complete) in bed 14 and the "hot spot" is now at the upper exit end of bed 14, which now has a temperature of 210° C. Vaporisation of the aldehyde from line 20 in vaporisation zone 19 results in an inlet temperature to bed 24 of 180° C. The "hot spot" is still at the exit end of bed 24 which is now at 245° C. As this is only 5° C. higher than at the start of catalyst life, the increase in production of byproduct ester will be minimal. The start of life operating conditions are shown as a full line in FIG. 3, whilst the end of life operating conditions are shown as a broken line therein.

The plant operator can select the optimum proportions of the aldehyde to be supplied through lines 13 and 20 by monitoring the temperature rise across catalyst bed 36. If this temperature rise exceeds about 5° C. then this indicates that the amount of aldehyde breaking through bed 24 is increasing, due to catalyst activity declining in bed 24, with a corresponding risk of increase in the "hot spot" temperature in bed 36 and in byproduct ester formation. He can then decrease the flow of aldehyde in line 20 and increase correspondingly the flow of aldehyde in line 13 until the desired temperature rise across catalyst bed 36 is again achieved.

Figure 4:
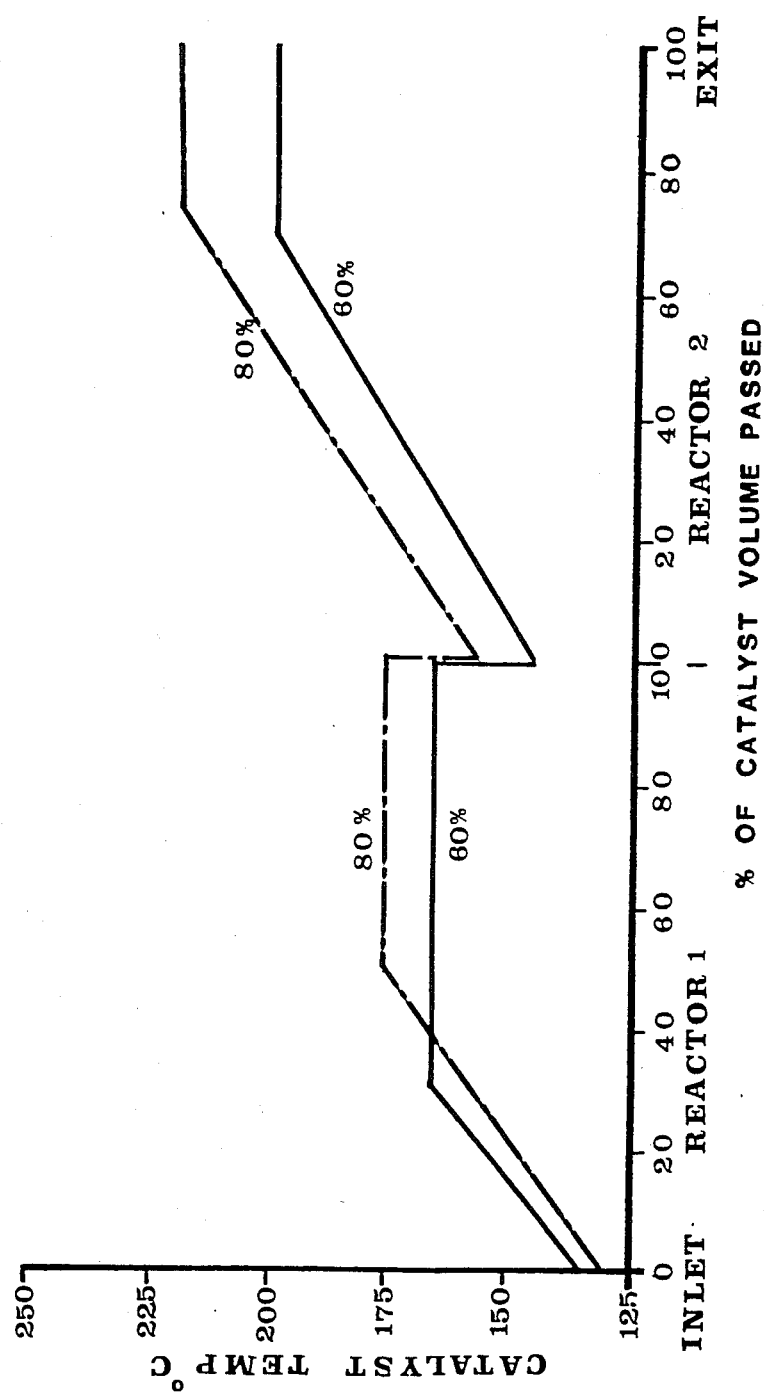
Figure 5:
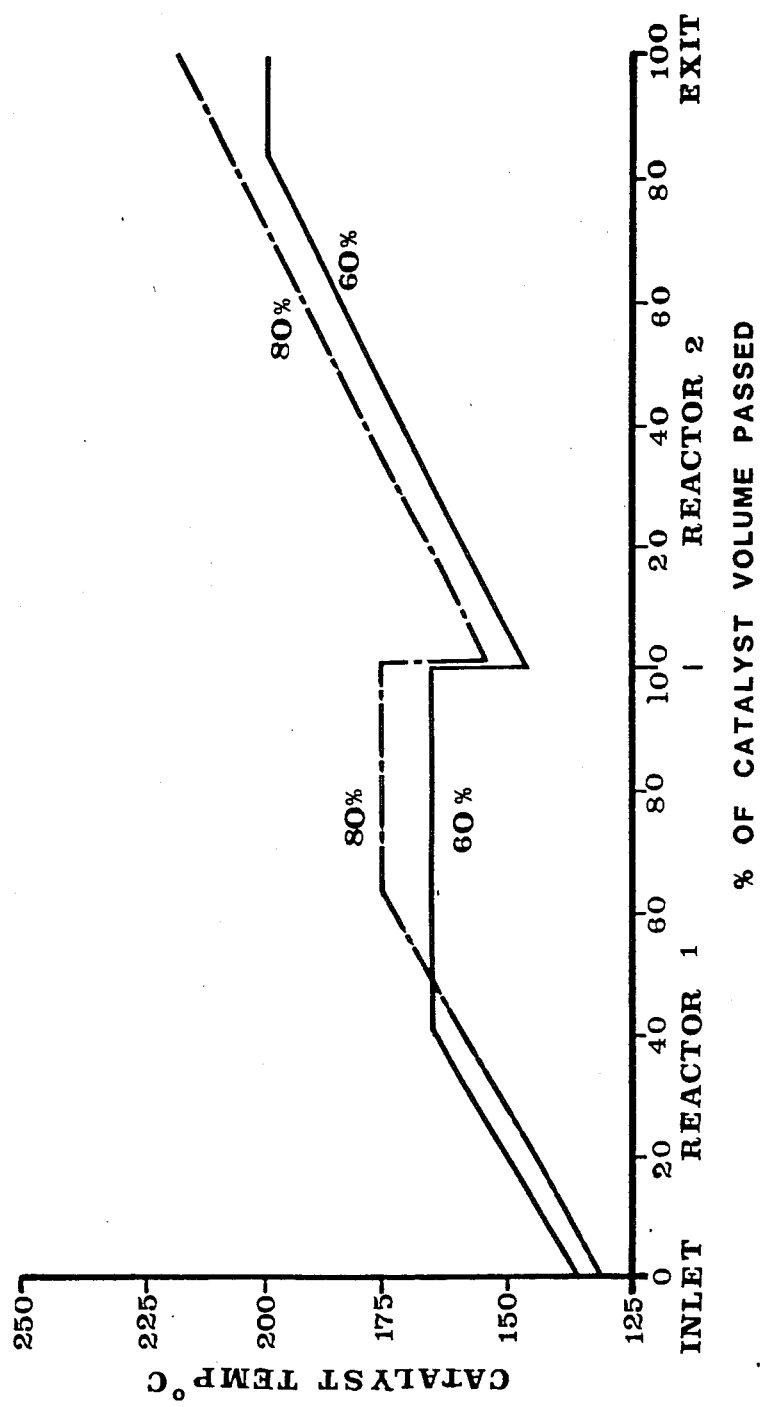

At full capacity the aldehyde fed in line 20 is vaporised and superheated using the heat of reaction generated in catalyst bed 14 and contained as sensible heat in the stream in line 15. Under turndown conditions the amounts of aldehyde fed through each of lines 13 and 20 will be reduced, as it will not be possible to vaporise the full normal feed of aldehyde supplied in line 20 (i.e. 62.5% of the total aldehyde) without feeding some aldehyde via line 13 to the first catalyst bed 14 in order to provide the latent heat of vaporisation to vaporiser 19. At 60% overall throughput, for example, 15% of the design feed to the plant is supplied in line 13 whilst the remaining 45% of the design feed is fed in line 20. As the catalyst bed 24 is designed to react 62.5% of the design feed of aldehyde at the start of catalyst life, there will be some surplus catalyst at the exit end of catalyst bed 24, though most of the surplus catalyst will be in the first bed 14. At 80% overall throughput the feed split would be about 30% in line 13 and 50% in line 20. The temperature gradients in beds 14 and 24 at the start of catalyst life are shown for 60% design throughput as a full line in FIG. 4 and for 80% design throughput as a broken line in FIG. 4. The corresponding gradients at the end of catalyst life are shown in FIG. 5; again the 60% design throughput case is shown as a full line, whilst the 80% design throughput situation is designated by a broken line.

Using this mode of turndown some increase in byproduct formation will occur as a consequence of having to perform some reaction in catalyst bed 14 in order to vaporise the aldehyde feed to vaporiser 19, resulting in ester formation over the surplus catalyst at high temperature at the exit end of catalyst bed 24.

Figure 6:
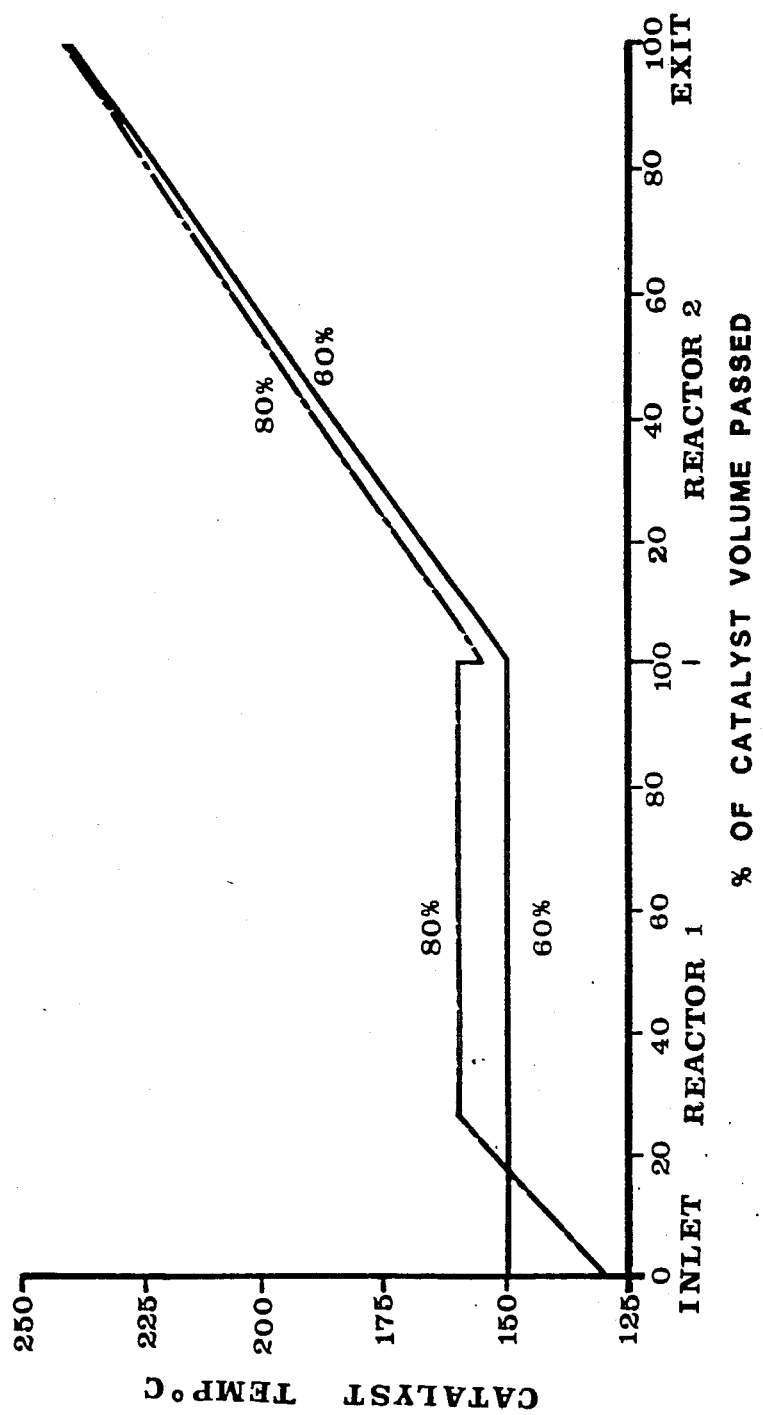

Alternatively, instead of relying on the heat generated in catalyst bed 14 to vaporise the aldehyde feed to vaporiser 19 under turndown conditions, the aldehyde feed in line 20 can be passed through preheater 52. By use of preheater 52 a reduction in throughput can be achieved by reducing the feed in line 13 only. Using this mode of operation at 80% design throughput there is no surplus catalyst in the catalyst bed 24, the surplus catalyst being contained in bed 14 where, because of the low aldehyde feed rate in line 13, the temperature rise is low and the rate of byproduct ester formation is low. Hence the overall rate of byproduct ester formation is correspondingly low. At 60% design throughput all the aldehyde can be fed in line 20 and none through line 13. At the start of catalyst life the temperature profile at 60% design throughput in this case is shown as a full line in FIG. 6, whilst the corresponding temperature profile for 80% design throughput is shown as a broken line. At 60% design throughput, no ester byproduct is formed in bed 14 if no aldehyde is fed to it and little is formed in bed 24 as the dwell time of the product mixture at temperatures above about 200° C. therein is very short.

In either case the feed rate of aldehyde in line 20 is shown to effect about 95% hydrogenation in passage through bed 24. For the 80% design throughput case, 17.5% of the aldehyde is fed through lines 13 and 62.5% in line 20.

It will thus be seen that the plant illustrated in FIG. 1 offers the plant operator considerable flexibility in operation and yields an acceptably low amount of byproduct under a wide variety of operating conditions.

Whilst it will be appreciated by those skilled in the art that some advantage would accrue, compared with conventional single stage aldehyde hydrogenation plants, if two catalytic stages only connected in series were used, the first of which was operated under adiabatic conditions and was used to hydrogenate the the bulk, for example about 95%, of the feed aldehyde, whilst the second stage was used to hydrogenate the remaining chemically unsaturated material remaining in the cooled intermediate product mixture from the first stage, it will be recognised that such an arrangement would not offer the plant operator the great operating flexibility described above that enables operation under optimal conditions under a wide variety of operating conditions. Such flexibility of operation requires on the contrary the use, according to the invention, of at least three catalytic stages connected in series.

In FIG. 1 the 2-ethylhexanol recycle line 52 is connected to the top of the respective vaporisation zone 8 or 19. FIG. 7 shows an alternative design of vessel to replace vessel 7. In FIG. 7 the same reference numerals have been used to indicate like parts to those used in FIG. 1. Vessel 56 is generally similar to vessel 7 but has, in place of a single packed vaporisation zone 8, a pair of similar packed vaporisation zones 57 and 58. Recycled 2-ethylhexanol from line 52 is sprayed onto zone 57, whilst 2-ethylhex-2-enal feed is sprayed on top of the packing of zone 58-from line 13. Reference numeral 59 indicates a spray eliminator pad. By-passed gas from line 9 is admixed with the ascending vaporous mixture above pad 59.

A vessel similar to vessel 56 can also be used in place of vessel 18 in the plant of FIG. 1.

The plant of FIG. 1 and the operating techniques described above are generally applicable to hydrogenation of organic materials in the vapour phase and provide, in particular, operating and capital cost advantages in cases in which the exposure of the organic feed or product materials to the catalyst at high temperatures tends to cause the formation of undesirable byproducts. It will accordingly be readily apparent to the skilled reader that the teachings of the invention can be practised with a wide variety of hydrogenation reactions other than the aldehyde hydrogenation reactions specifically described in relation to the accompanying drawings.

What is claimed is:

1. A continuous process for the catalytic hydrogenation of an unsaturated organic compound to a hydrogenation product thereof which comprises:
   providing a catalytic hydrogenation zone comprising (i) a first catalytic stage, (ii) at least one intermediate stage, including a penultimate stage, and (iii) a final catalytic stage, each stage containing a charge of a hydrogenation catalyst and the stages being connected in series so that material from one stage is fed to the next stage in the series;
   supplying to the first catalytic stage, at a first preselected rate and at a temperature at least as high as the threshold temperature for the hydrogenation reaction, a first vaporous feed mixture comprising excess hydrogen and the unsaturated organic compound;
   allowing catalytic hydrogenation to occur substantially adiabatically in the first catalytic stage;
   recovering from the, or from each, catalytic stage preceding the penultimate catalyst stage in the series a corresponding vaporous product mixture containing hydrogenation product and excess hydrogen;
   vaporising in the, or in each, resulting vaporous product mixture a preselected amount of further unsaturated organic compound to form a corresponding vaporous feed stream for supply to the next catalytic stage in the series;
   supplying to the, or to each, intermediate catalytic stage, at a corresponding preselected rate and at a temperature at least as high as the threshold temperature for the hydrogenation reaction, a corresponding intermediate vaporous feed stream comprising a mixture of further vaporous unsaturated organic compound and product mixture from the preceding catalytic stage of the series;
   allowing hydrogenation to occur substantially adiabatically in the, or in each, intermediate catalytic stage;
   controlling the rate of supply of, and the composition of, the corresponding intermediate vaporous feed stream fed to the penultimate catalytic stage in relation to the volume of catalyst therein so that, under the substantially adiabatic conditions prevailing in the penultimate catalytic stage, the product mixture recovered therefrom still contains a minor amount of chemically unsaturated material;
   recovering from the penultimate catalytic stage a vaporous penultimate product mixture containing hydrogenation product, a minor amount of chemically unsaturated material and excess hydrogen;
   cooling the vaporous penultimate product mixture;
   supplying resulting cooled penultimate product mixture containing hydrogenation product, a minor amount of chemically unsaturated material and hydrogen to the final catalytic stage at a temperature at least as high as the threshold temperature for the hydrogenation reaction;
   allowing hydrogenation of the minor amount of chemically unsaturated material in the penultimate product mixture to occur substantially to completion in the final catalytic stage; and
   recovering from the final catalytic stage a final product mixture that contains hydrogenation product and excess hydrogen and is substantially free from chemically unsaturated material.

2. A process according to claim 1, in which the catalytic hydrogenation zone includes a single intermediate catalytic stage which forms the penultimate catalytic stage in the series, and in which the intermediate vaporous feed mixture to the intermediate catalytic stage comprises a mixture of further vaporous unsaturated organic compound and vaporous product mixture from the first catalytic stage.

3. A process according to claim 1, which includes the step of controlling the rate of supply of, and the composition of, the feed mixture to the, or to each, catalytic stage proceeding the penultimate stage in the series in relation to the volume of the catalyst therein so that, under the substantially adiabatic conditions prevailing therein, the product mixture recovered therefrom still contains a minor amount of chemically unsaturated material.

4. A process according to claim 1, in which the entry temperature to the first catalytic stage and the entry temperature to the, or to each, intermediate catalyst stage is, in each case, at least about 5° C. to about 15° C. above the dew point of the corresponding vaporous feed mixture.

5. A process according to claim 1, in which the cooled penultimate product mixture is supplied in vaporous form to the final catalytic stage.

6. A process according to claim 5, in which the entry temperature to the final catalytic stage is at least about 5° C. to about 15° C. above the dew point of the mixture.

7. A process according to claim 1, in which the cooled penultimate product mixture is supplied in liquid form to the final catalytic stage.

8. A process according to claim 1, in which hydrogenation of the chemically unsaturated material in the penultimate product mixture is allowed to occur substantially adiabatically in the final catalytic stage.

9. A process according to claim 1, in which the unsaturated organic compound is an aldehyde and the hydrogenated product is an alcohol.

10. A process according to claim 9, in which the aldehyde is propionaldehyde, in which the chemically unsaturated material is also propionaldehyde, and in which the alcohol is n-propanol.

11. A process according to claim 9, in which the aldehyde is n-butyraldehyde, in which the chemically unsaturated material is also n-butyraldehyde, and in which the alcohol is n-butanol.

12. A process according to claim 9, in which the aldehyde is 2-ethylhex-2-enal, in which the chemically unsaturated material is selected from 2-ethylhex-2-enal, 2-ethylhex-2-enal, 2-ethylhexanol, and mixtures of two or more thereof, and in which the alcohol is 2-ethylhexanol.

13. A process according to claim 9, in which the entry temperature to the first catalytic stage lies in the range of from about 90° C. to about 220° C. and in which the pressure in the first catalytic stage lies in the range of from about 5 to about 50 bar.

14. A process according to claim 9, in which the entry temperature to the penultimate catalytic stage lies in the range of from about 120° C. to about 220° C. and in which the pressure in the penultimate catalytic stage lies in the range of from about 5 bar to about 50 bar.

15. A process according to claim 9, in which the entry temperature to the final catalytic stage is in the range of from about 120° to about 220° C. and in which the pressure in the final catalytic stage lies in the range of from about 5 bar to about 50 bar.

16. A process according to claim 1, in which a part of the hydrogenated product recovered from the final product mixture is recycled for vaporisation in at least one of the vaporous streams.

17. A process according to claim 1, in which the step of controlling the rate of supply of, and the composition of, the corresponding intermediate vaporous stream fed to the penultimate catalytic stage includes the steps of monitoring the temperature rise across the final catalytic stage and adjusting the preselected amount of unsaturated organic compound that is vaporised in the vaporous product mixture from the ante-penultimate catalytic stage so that the temperature rise across the final catalytic stage lies within a predetermined range.

18. A process according to claim 1, in which the overall rate of supply of unsaturated organic compound to the catalytic hydrogenation zone is reduced to a rate that is less than the design capacity of the plant and in which any reduction in the rate of supply of unsaturated organic compound to the penultimate catalytic stage from the respective flow rate thereto at design capacity is proportionately significantly less than any corresponding reduction in the rate of supply of unsaturated organic compound to any preceding catalytic stage from the respective flow rate thereto at design capacity.

19. A continuous process for the catalytic hydrogenation of an unsaturated organic compound to a hydrogenation product thereof which comprises:

providing a catalytic hydrogenation zone comprising first, second and third catalytic stages connected in series, each containing a charge of a hydrogenation catalyst;

supplying to the first catalytic stage, at a first preselected rate and at a temperature at least as high as the threshold temperature for the hydrogenation reaction, a first vaporous feed stream comprising excess hydrogen and the unsaturated organic compound;

allowing catalytic hydrogenation to occur substantially adiabatically in the first catalytic stage;

recovering from the first catalytic stage a vaporous first product stream containing hydrogenation product and excess hydrogen;

vaporising in the first product stream a preselected amount of further unsaturated organic compound to form a second vaporous feed stream;

supplying the second vaporous feed stream to the second catalytic stage at a second preselected rate and at a temperature at least as high as the threshold temperature for the hydrogenation reaction, the preselected amount being so chosen in relation to the volume of the catalyst charge in the second catalytic stage and to the second preselected rate that, upon allowing hydrogenation to occur substantially adiabatically in the second catalytic stage, the product mixture recovered therefrom still contains a minor amount of chemically unsaturated material;

allowing hydrogenation to occur substantially adiabatically in the second catalytic stage;

recovering from the second catalytic stage a vaporous second product mixture containing hydrogenation product, a minor amount of chemically unsaturated material and excess hydrogen;

cooling the vaporous second product mixture;

supplying a third feed stream comprising cooled second product mixture to the third catalytic stage at a temperature at least as high as the threshold temperature for the hydrogenation reaction;

allowing hydrogenation of the minor amount of chemically unsaturated material in the second product mixture to occur substantially to completion in the third catalytic stage; and recovering from the third catalytic stage a third product mixture that contains hydrogenation product and excess hydrogen and that is substantially free from chemically unsaturated material.

20. A process according to claim 19, in which the first preselected rate is so chosen in relation to the volume of the catalyst charge of the first catalytic stage that, upon permitting hydrogenation to proceed under substantially adiabatic conditions in the first catalytic stage, the vaporous first product mixture contains, in addition to hydrogenation product and excess hydrogen, also a minor amount of chemically unsaturated material.

21. A process according to claim 19, in which the third feed stream is in vaporous form.

22. A process according to claim 19, in which the third feed stream is in liquid form.

23. A process according to claim 19, in which the unsaturated organic compound is an aliphatic aldehyde and the saturated product is an alcohol.

24. A process according to claim 23, in which the aliphatic aldehyde is n-butyraldehyde, in which the chemically unsaturated material is also n-butyraldehyde, and in which the saturated product is n-butanol.

25. A process according to claim 23, in which the aliphatic aldehyde is 2-ethylhex-2-enal, in which the chemically unsaturated material is selected from 2-ethylhex-2-enal, 2-ethylhex-2-enol, 2-ethylhexanal, and mixtures of two or more thereof and in which the saturated product is 2-ethylhexanol.

26. A process according to claim 19, in which the catalyst consists essentially of a reduced mixture of CuO and ZnO.

27. A process according to claim 19, in which the entry temperature of each vaporous feed mixture to the corresponding catalytic stage is at least about 5° C. to about 15° C. above its dew point.

28. A process according to claim 19, in which a part of the hydrogenation product recovered from the third catalytic stage is recycled for vaporisation in at least one of the first and second feed mixtures.

29. A process according to claim 19, in which the overall rate of supply of unsaturated organic compound to the catalytic hydrogenation zone is less than the design capacity of the plant and in which the rate of supply of unsaturated organic compound to the first catalytic stage is reduced proportionately in relation to the respective rate at design capacity significantly more than any corresponding reduction in rate of supply of unsaturated organic compound to the second catalytic stage.

30. A continuous process for the catalytic hydrogenation of an aldehyde which may contain one or more unsaturated carbon-carbon bonds to a corresponding alcohol which comprises:

providing a catalytic hydrogenation zone comprising n catalytic stages in series, where n is an integer of at least 3, each catalytic stage containing a charge of a solid hydrogenation catalyst effective for catalytic hydrogenation of aldehydes;

supplying to the first catalytic stage a first vaporous mixture comprising excess hydrogenation and the aldehyde at a first temperature which is equal to, or is in excess of, the threshold temperature for the hydrogenation reaction;

allowing catalytic hydrogenation to occur substantially adiabatically in each catalytic stage up to and including the $(n-1)$th catalytic stage, thereby to effect hydrogenation to corresponding alcohol of aldehyde supplied to that stage;

vaporising further aldehyde in the vaporous product mixture from the, or from each, mth catalytic stage in the series, where m is an integer equal to or less then $(n-2)$, to form a corresponding vaporous feed mixture for supply to the corresponding $(m+1)$th catalytic stage in the series;

supplying resulting vaporous feed mixture to the corresponding $(m+1)$th catalytic stage at a temperature which is equal to, or is an excess of, the threshold temperature for the hydrogenation reaction;

controlling the rate of supply of, and the composition of, the corresponding vaporous feed stream to the $(n-1)$th catalytic stage in relation to the volume of catalyst therein so that, under the substantially adiabatic conditions prevailing in the $(n-1)$th catalytic stage, the product mixture recovered therefrom still contains a minor amount of chemically unsaturated material;

recovering from the $(n-1)$th catalytic stage a vaporous product mixture containing product alcohol, a minor amount of chemically unsaturated material, and excess hydrogen;

cooling the product mixture from the $(n-1)$th catalytic stage;

supplying cooled product mixture form the $(n-1)$th catalytic stage to the nth catalytic stage at the temperature which is equal to, or in excess of, the threshold temperature for the hydrogenation reaction;

allowing hydrogenation to proceed substantially to completion in the nth catalytic stage; and recovering from the nth catalytic stage a final vaporous product mixture that contains the corresponding product alcohol and that is substantially free from chemically unsaturated material.

* * * * *